United States Patent [19]

Martin

[11] Patent Number: 4,673,400
[45] Date of Patent: Jun. 16, 1987

[54] ASEPTIC CONNECTOR ASSEMBLY FOR CONDUITS FOR STERILE FLUIDS

[76] Inventor: Ivan W. Martin, R.D. 4—Box 156A, Denver, Pa. 17517

[21] Appl. No.: 827,459

[22] Filed: Feb. 10, 1986

[51] Int. Cl.$^4$ .............................................. A61M 3/00
[52] U.S. Cl. ..................................... 604/283; 604/905
[58] Field of Search .................. 604/283, 265, 28, 29, 604/905

[56] References Cited

U.S. PATENT DOCUMENTS

| | | |
|---|---|---|
| 2,689,562 | 9/1954 | Adams et al. . |
| 4,019,512 | 4/1977 | Tenczar . |
| 4,022,205 | 5/1977 | Tenczar . |
| 4,161,949 | 7/1979 | Thanawalla . |
| 4,209,013 | 6/1980 | Alexander et al. ................... 604/29 |
| 4,369,781 | 1/1983 | Gilson et al. . |
| 4,432,764 | 2/1984 | Lopez .............................. 604/283 |
| 4,432,766 | 2/1984 | Bellotti et al. ....................... 604/283 |

*Primary Examiner*—C. Fred Rosenbaum
*Assistant Examiner*—Sherri E. Vinyard

[57] ABSTRACT

A simplified aseptic connector assembly for tubes or conduits to conduct sterile fluids and comprising interconnectable complementary male and female connector members respectively connectable to the ends of tube sections to be connected, one of the members having a socket open at one end and dimensioned to slidably receive the other member which also has an axial socket open at the outer end which is adapted to be received in the socket of the one member, the axial socket in the other member being tapered and complementary in shape to a tubular prong extending axially within the socket of the one member for frictional reception within the tapered socket of the other member and the prong having a piercing tip terminating short of the open face of the open end of one member, each of the open ends of the sockets of the members initially being sealed by membranes to maintain the interiors of the sockets in aseptic condition; the sealed ends of the connector members being adapted to be dipped in a disinfecting solution and then abutted firmly to maintain sterility, followed by telescopically inserting the other member into the socket of the one member initially to cause the piercing prong to pierce both membranes and then establish the prong in firm fricitonal engagement within the tapered socket in the other member to establish a passage between tubes connected by the connector members.

6 Claims, 3 Drawing Figures

ASEPTIC CONNECTOR ASSEMBLY FOR CONDUITS FOR STERILE FLUIDS

BACKGROUND OF THE INVENTION

This invention relates to the production of aseptic connectors for connecting in a sterile manner conduits or tubes extending between two bodies, one body and a container, two containers, or otherwise to create an aseptic juncture therebetween for the flow of sterile fluid through said connectors which, essentially, comprise an aseptic connector assembly.

Aseptic connectors and assemblies thereof are well-known. A variety of different designs have been developed heretofore in attempts to assure that when the connectors are used for the aseptic transfer of sterile fluids or the like, such fluids will remain sterile and aseptic. Heretofore, a popular approach has been to utilize membranes penetrated by a piercing point on a prong or spike on the end of a tube which is to receive the fluid. Usually, the membrane is in the form of a flexible sleeve closed at one end and inerted over the prong or spike, needle or otherwise. One example of this type of device comprises the subject matter of prior U.S. Pat. No. 2,689,562 to Adams et al, dated Sept. 21, 1954. One problem inherent to such type of device is that if the spike is used to penetrate receiving membrane and becomes contaminated before the membrane is broken, the spike may contaminate fluid passing through a connector and, in various situations, slidably removable caps placed over spikes or needles heretofore have not proved adequate to maintain the spikes in an aseptic condition since such caps may easily be accidentally or intentionally removed by personnel prior to the time for the connectors to be used, with contamination of the spike possibly resulting.

More recent means to effect connection between two tubes or conduits for sterile fluid comprises the subject matter of U.S. Pat. No. 4,019,512, dated Apr. 26, 1977, and U.S. Pat. No. 4,022,205, dated May 10, 1977, both in the name of Tenczar. The first of these patents is quite complex and includes a pair of telescopic socket members respectively having abutting surfaces at the open ends which are initially sealed by a pair of pressure-sensitive membranes initially covered by protecting films capable of being laterally removed, and then the socket members continue to move toward each other to cause a piercing means in the socket of one member acting to pierce the membranes which are connected by pressure-sensitive cement. The second of these patents is directed to connecting means which are less complex than the first and include a pair of sockets which initially are covered by a pair of membranes, connectable by a pressure-sensitive cement if desired and covered by protecting, removable membranes and when the first mentioned membranes are placed in abutment, a tubular member axially movable within the sleeve in one of the sockets and terminates in a piercing point, is pushed through the connected membranes to effect communication between the sockets. Various coaxial sleeve means respectively in the two sockets also are movable into overlapping position.

Still another patent, U.S. Pat. No. 4,161,949, to Thanawalla, dated July 24, 1979, is directed to an aspetic connector in which two telescopically-related members initially are covered by membranes and additional telescopical-arranged tubes, coaxial with the walls of the main socket members are moved coaxially to pierce the sealing membranes to effect an aseptic connection between the socket members.

Still another relatively recent, prior U.S. Pat. No. 4,369,781, to Gilson et al, dated Jan. 25, 1983, in a general way shows the use of a tapered connection between male and female members and including a flexible, slotted diaphragm of metal through which one of the telescopic members projects to engage a socket in the other member.

In general, the present invention comprises structure which is substantially more simple and therefore, less expensive to manufacture than the devices illustrated in the aforementioned patents and, simultaneously, provides what is believed to be connection means which are superior to, as well as more simple than the prior art devices referred to above, while providing as high, if not a higher degree of asepticism than the devices previously developed, while simultaneously providing greater ease of operation than at least certain of the prior art devices, details of which are set forth below.

SUMMARY OF THE INVENTION

It is among the principal objectives of the present invention to provide complementary male and female connector members comprising an assembly adapted to be associated with a pair of tubes or conduits through which sterile fluid is to be passed and sterility thereof maintained during such passage through the connected members, said male and female connector members respectively being provided with sockets initially open at the outer end thereof and covered by sealing membranes which maintain the interior of said sockets in aseptic condition, and said sealed ends of said connector members being dipped in an antiseptic solution for an adequate period of time to render the outer surfaces of the membranes aseptic and, when withdrawn from immersion in the antiseptic solution, the membranes are placed in abutting relationship and maintained in such position for a limited period of time adequate to insure a sterile phase between the abutted surfaces of the membranes, following which the male member is pushed into the socket of the female member telescopically and the female member having a tubular prong terminating in a piercing tip disposed coaxially therein and adapted to be received in the socket of the male member in firm frictional manner, the telescopic connection of the two members resulting in the piercing point of the prong and the female member piercing both of the abutted membranes in a manner to maintain the coengagement of the connector members sterile.

It is another object of the invention to provide the prong in the female connector member with a longitudinal passage terminating interiorally adjacent the piercing point and said prong being tapered similarly to the socket in the male member which telescopically receives said prong in a tight, frictional manner to maintain connection between the two connector members.

A further object of the invention is to provide each of the connector members on the ends opposite the socketed ends with tubular extensions readily adapted to be connected to conduits or tubes in conventional manner.

Still another object of the invention is to arrange the length of the male connector member so that when it is fully inserted into the socket of the female member and the tapered prong and socket respectively therein are in firm frictional engagement, the innermost end of the male member is spaced a limited distance from the inner end of the socket in the female member so as to minimize the possiblity of the frictional connection of said prong and socket not being achieved.

Details of the foregoing objects and of the invention, as well as other objects thereof, are set forth in the following specification and illustrated in the accompanying drawings comprising a part thereof.

DETAILED DESCRIPTION OF THE PREFERRED EMBODIMENT

Figure 1:
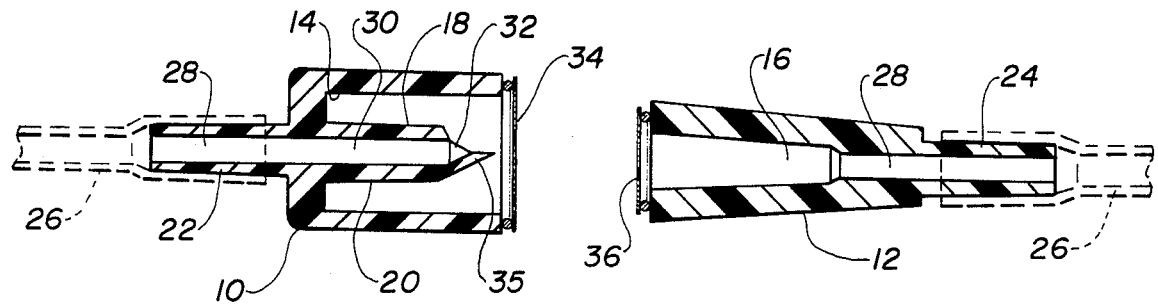
FIG. 1 is a longitudinal sectional composite view, showing the male and female connector members of the invention with the sealed ends of the sockets therein adjacent each other and in position to effect longitudinal connecting movement between the two members, said figure also showing in phantom fragmentary ends of tubes connected to and extending from the outer ends of the members.

Referring to FIG. 1, it will be seen that the connector assembly comprising the present invention includes a female connector member 10 and a male connector member 12, both of which are shown in longitudinal section. One end of the female member 10 has a substantially cylindrical socket 14 and the corresponding end of the male connector member 12 has a socket 16, which is tapered for purposes of telescopically and tightly receiving a tubular prong or spike 18, which on the exterior has a tapered surface 20 that is very closely complementary to the taper of the socket 16 in which it is received, as described below. The opposite ends of the male and female connector members 10 and 12 are each provided with tubular means 22 and 24 to which respectively one end of exemplary tubes or conduits 26, shown in phantom, are connected. Socket 16 and spike 18 comprise a luer fitting.

The male and female connectors 10 and 12 thus far described preferably are formed relatively inexpensively by injection molding the same from suitable, preferably rigid plastic material. The thus molded members include longitudinal passages 28 coaxially within the aforementioned outer ends of the members 10 and 12, the passage 28 in male member 12 communicating with the socket 16 therein and the passage 28 within the female socket 10 is a continuation of the tubular passage 30 within the prong 18. Said passage terminates in an opening 32 formed in piercing point 35. From the foregoing, it will be seen that all elements thus far described with respect to both the male and female connector members 10 and 12 are integral. The outer end of the male connector member 12 has a diameter only slightly less than the inner diameter of cylindrical socket 14 in female connector member 10 in order that the outer end of the male member 12 readily may slide along the interior surface of the socket 14.

From FIG. 1, it will be seen that the sockets 14 and 16 are open at the outer ends thereof as manufactured, and in order to maintain the interiors of the sockets sterile prior to use, said open outer ends thereof are sealed respectively by very thin, impervious membranes 34 and 36, which are firmly connected to the walls defining the open ends of the sockets 14 and 16 of members 10 and 12. Suitable cement, shown in FIG. 1 by a dot, effects the sealed connection of each membrane to the end of the socket to which it is affixed. Said membranes may be of an appropriate impervious metal or plastic nature, preferably not in excess of three microns in thickness, the preferred thickness being approximately one and one-half microns in thickness. It is to be understood that when manufactured, the male and female connector members 10 and 12 preferably are sold in sterile packages in which they are hermetically sealed. Connection of tubes or conduits to the tubular means 22 and 24 on said members is undertaken in sterile manner of appropriate nature, while the interior of the sockets 14 and 16 in the connector members remain sterile.

METHOD OF OPERATION

Figure 2:
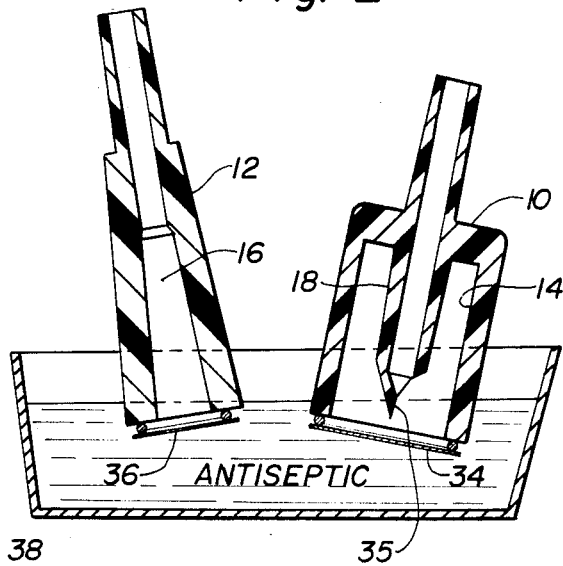
FIG. 2 is a diagrammatic vertical sectional view of the connector member shown in FIG. 1, positioned with the sealed ends thereo immersed in an antiseptic solution for purposes of sterilizing the sealed ends of said members.

Assuming that the connector members 10 and 12 have been connected to tubes or conduits 26 in sterile manner, and connection of the connector members 10 and 12 is desired to be undertaken, reference is made to FIG. 2 in which it will be seen, at least diagrammatically, that the sealed ends of members 10 and 12 upon which the membranes 34 and 36 have been attached, are immersed in an appropriate antiseptic solution, which may be of a number of different types, such as denatured or medical alcohol, povidone iodine or other suitable solutions capable of rendering the exterior surfaces of the diaphragms 34 and 36 aseptic. Immersion of the diaphragms in the solution 38 extends for a limited, but nevertheless, satisfactory period of time to insure an aseptic outer surface of each diaphragm, which period may be of the nature of five or ten seconds, or more. The sealed ends of the connector members then are withdrawn from the solution and while still wet therewith, the outer surfaces of the diaphragms are firmly abutted together and maintained in such manner for another suitable period of time, such as possibly five or ten seconds before longitudinal movement of the connector members toward each other is undertaken. Such movement may be relatively quick, however, and the male member 12 is inserted within the cavity 14 of the female member 10 substantially to full extent, as shown in exemplary manner in FIG. 3. Such insertion, however, is limited by engagement of the outer surface of the prong 18 with the interior walls of the socket 16 in the male member 12, as also shown in FIG. 3, and the length portion of the male member 12 which is inserted into the socket 16 is such that a limited clearance space 40 is provided at said inner end of the male member 12 with respect to the inner end of the socket 14 in the female member so as to insure firm frictional engagement between the tapered socket 16 by the tapered tubular prong 18, and such frictional engagement is adequate to maintain the two connector members in suitable operative connected position for practical purposes.

Figure 3:
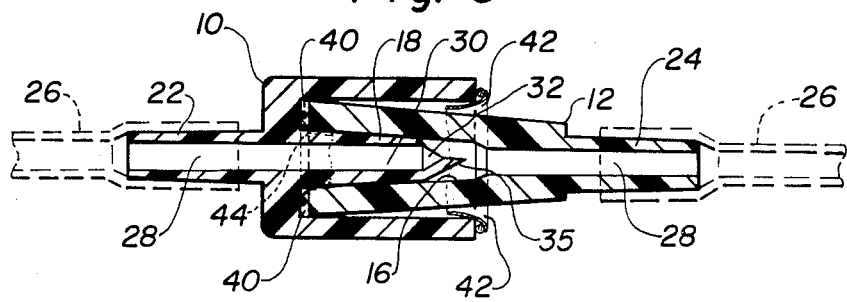
FIG. 3 is a view similar to FIG. 1 but illustrating the connector members in fully connected relationship after the sealed ends thereof have been sterilized and the connection between the members being aseptic in nature.

During the initial part of the insertion of the male member 12 within the cavity 14 of the female member, diaphragm 34 is burst and fragmentary portions 42 of diaphragm 34 are disposed among the inner surfaces of the outer end of socket 14 in the female member as shown fragmentarily in FIG. 3. Similarly, fragmentary portions 44 of diaphragm 36 are disposed tightly between the frictionally connected prong 18 and socket 16, as shown in FIG. 3. This is made possible due to the very thin nature of the diaphragm 36, and in no way interferes with the frictional connection between the prong 18 and socket 16.

At the conclusion of the full insertion of the male member 12 within the cavity 14 of the female member, as illustrated in FIG. 3, a continuous aseptic passage is established between the tubes or conduits 26, which are connected to opposite ends of the connected connector members 10 and 12, such continuous passage including the longitudinal passages 28, tubular passage 30 in prong 18 and opening 32 in the piercing point 34.

From the foregoing, it will be seen that the male and female connector members 10 and 12 comprising the present invention, together with the sealing membranes 34 and 36 thereon, comprise a highly effective, but nevertheless, extremely simple assembly to effect an aseptic connection between conduits to which said connector members are affixed by utilizing a very simple step of sterilizing the exterior surfaces of the sealing diaphragms prior to abutting the same and then telescopically moving the male connector member substantially fully into the socket of the female connector member, a highly sterile connection is made not only between the two connector members, but also between the conduits or tubes to which they respectively are connected.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. An aseptic connector assembly for connecting conductors for sterile fluids comprising in combination, axially extending complementary male and female connector members each having tubular means integral therewith at one end and connectable to a conductor, the female member also having an axial socket on the opposite end, opening outwardly and dimensioned to slidably receive said male member longitudinally, the male member also having a tapered axial socket on the opposite end thereof opening outward and communicating with the tubular means on said one end thereof, the socket of said female member also having an axially-extending prong integral therewith and terminating in a piercing point spaced inwardly from the plane of the open end of the socket and being tapered in complement to the taper of the socket of said male member and adapted to frictionally engage said socket when inserted thereinto, and sterile sealing membranes aseptically and respectively affixed over the outer ends of both of said sockets; said sterile membranes and the outer ends of the sockets to which they are connected being adapted to be firmly abutted and the male member inserted within the female member initially to pierce the sterile membrane affixed over the face of the socket in the female member and followed by said piercing prong puncturing the membrane affixed over the face of the socket in said male member and finally frictionally engage said piercing prong within the tapered socket in said male member to establish a sterile fluid passage through the connected members.

2. The aseptic connector assembly according to claim 1 in which said piercing point is tubular and also has an opening communicating directly with the interior of the tubular configuration of said prong.

3. The aseptic connector assembly according to claim 1 in which the length of said male member is such that when said prong of the female member is in firm frictional engagement within the socket in said male member the end of the male member which is within the socket of the female member is spaced from the inner end of said socket in the female member.

4. The aseptic connector assembly according to claim 1 in which the thickness of at least the membrane which extends across and is attached to the open end of the socket in the male member is not appreciably in excess of three microns.

5. The aseptic connector assembly according to claim 4 in which the thickness of at least the membrane which extends across and is attached to the open end of the socket in the male members is substantially one and one-half micron.

6. The aseptic connector assembly according to claim 1 in which communication between said tubular means on said female member and the interior of the socket in said member is accomplished by the prong in said female member having a longitudinal passage therein and the piercing point of said prong having an opening therethrough in communication with said passage in said prong.

* * * * *